United States Patent
Liddy et al.

(10) Patent No.: US 9,861,919 B2
(45) Date of Patent: Jan. 9, 2018

(54) CELL COLLECTOR HAVING AN EXPANDABLE MESH

(71) Applicant: Cook Medical Technologies LLC, Bloomington, IN (US)

(72) Inventors: Alison Liddy, Blackrock (IE); Meurisse Leahy, Annacotty (IE); Michael Clancy, Monaleen (IE); Vincent McHugo, Birdhill (IE); Simon Brouwers, Amsterdam (NL)

(73) Assignee: Cook Medical Technologies LLC, Bloomington, IN (US)

( * ) Notice: Subject to any disclaimer, the term of this patent is extended or adjusted under 35 U.S.C. 154(b) by 597 days.

(21) Appl. No.: 14/212,280

(22) Filed: Mar. 14, 2014

(65) Prior Publication Data
US 2014/0263032 A1    Sep. 18, 2014

Related U.S. Application Data (60) Provisional application No. 61/793,581, filed on Mar. 15, 2013.

(51) Int. Cl.
| | | |
|---|---|---|
| *B01D 39/08* | (2006.01) | |
| *A61B 10/02* | (2006.01) | |
| *A61B 17/00* | (2006.01) | |
| *A61B 17/221* | (2006.01) | |

(52) U.S. Cl.
CPC ............ *B01D 39/086* (2013.01); *A61B 10/02* (2013.01); *A61B 10/0266* (2013.01); *A61B 2017/00867* (2013.01); *A61B 2017/2212* (2013.01); *Y10T 29/49817* (2015.01)

(58) Field of Classification Search
CPC . B01D 39/086; Y10T 29/49817; A61B 10/02; A61B 10/0266; A61B 2017/2212; A61B 2017/00867
USPC ....... 210/499, 435, 483, 470, 478, 645, 782; 606/200
See application file for complete search history.

(56) References Cited

U.S. PATENT DOCUMENTS

| | | | |
|---|---|---|---|
| 2,701,559 A | 2/1955 | Cooper | |
| 4,157,709 A | 6/1979 | Schuster et al. | |
| 4,227,537 A | 10/1980 | Suciu et al. | |
| 4,465,072 A | 8/1984 | Taheri | |
| 5,738,109 A | 4/1998 | Parasher | |
| 6,936,013 B2 | 8/2005 | Pevoto | |
| 2004/0059253 A1 | 3/2004 | Martone et al. | |
| 2004/0111111 A1* | 6/2004 | Lin | A61F 2/013 606/200 |
| 2004/0260201 A1 | 12/2004 | Mueller, Jr. | |
| 2005/0256426 A1 | 11/2005 | Brugge | |
| 2005/0277847 A1 | 12/2005 | Belinson | |
| 2008/0033482 A1* | 2/2008 | Kusleika | A61F 2/01 606/200 |
| 2008/0188769 A1 | 8/2008 | Lu | |

(Continued)

*Primary Examiner* — Madeline Gonzalez
(74) *Attorney, Agent, or Firm* — Brinks Gilson & Lione (57) ABSTRACT

A cell collection device having an elongated member and a mesh disposed about the elongated member. The mesh has a low energy expanded state and a high energy compressed state. A sheath is disposed about a distal end of the elongated member and is slidable along the elongated member from a first position in which the sheath radially constrains the mesh to the high energy compressed state and a second position in which the sheath does not constrain the mesh.

5 Claims, 5 Drawing Sheets

(56) References Cited

U.S. PATENT DOCUMENTS

2010/0234763 A1 9/2010 Valdmann et al.
2011/0021950 A1 1/2011 Daniels

* cited by examiner

CELL COLLECTOR HAVING AN EXPANDABLE MESH

RELATED APPLICATIONS

The present patent document claims the benefit of the filing date under 35 U.S.C. §119(e) of Provisional U.S. Patent Application Ser. No. 61/793,581, filed Mar. 15, 2013, which is hereby incorporated by reference.

FIELD

Embodiments of the present invention relate to medical devices and more particularly to devices and methods for collecting cells in a body lumen.

BACKGROUND

It is useful to collect biological surface cells from internal lumens of the body. Such cells are useful for diagnostic procedures including the identification of predictive biomarkers that allow clinicians to predict future prognosis for a patient. In such diagnostic procedures, it is important that a large numbers of cells are collected from an area of interest while minimizing the collection of foreign cells in order to obtain an accurate diagnostic result. Ideally, the collection of the surface cells would occur with no damage to the body lumen.

A current method of collecting surface cells is to use a cytology brush. The cytology brush has stiff bristles that extend radially outward from an axis of the cytology brush, and in some examples the stiff bristles have hooks to retain cell samples. The cytology brush is delivered to the area of interest and then brushed against a surface of the body lumen, abrading cells from the surface and catching the cells within the bristles. The use of the cytology brush may result in bleeding where the lumen surface is abraded and is inefficient in its collection of surface cells. Accordingly, it would be useful to have an alternative to a cytology brush for the collection of surface cells in a body lumen.

SUMMARY

In one embodiment of the invention a cell collection device comprises an elongated member, a mesh, and a sleeve. The elongated member has a distal end, a proximal end, and an outside diameter. The mesh is comprised of a plurality of interwoven filaments biased to expand outward to a deployed diameter greater than the outside diameter of the elongated member. A first end of the mesh is secured about the elongated member and is fixed axially. A second end of the mesh is secured about the elongated member and is free to translate axially along the elongated member. The sleeve is disposed about the distal end of the elongated member and has a bore with an inside diameter greater than the outside diameter of the elongated member and less than the deployed diameter. The sleeve is axially slidable along the elongated member from a first position that radially constrains the plurality of interwoven filaments to a first configuration and a second position that does not radially restrain the plurality of interwoven filaments allowing the plurality of interwoven filaments to expand to the deployed diameter.

In another embodiment a cell collection device comprises a proximal tubular member, a braided portion, a distal tubular member, and a sheath. The proximal tubular member is comprised of an inner layer, an outer layer, and a braided layer disposed between the inner layer and the outer layer. The braided layer extends beyond a distal end of the proximal tubular member. The braided portion comprises a first portion of the braided layer extending beyond the distal end of the proximal tubular member and extends beyond a distal end of the braided portion. The distal tubular member comprises an inner layer, an outer layer, and a portion of the braided layer extending past distal end of the braided portion. The sheath is disposed about the distal end of the proximal tubular member and has a first position in which an inner surface of the sheath covers the braided portion and a second position in which the sheath does not cover the braided portion.

Another embodiment is directed to a method for manufacturing a cell collection device. In the method a multilayer catheter having an inner layer, an outer layer, and a braid comprised of a plurality of woven filaments disposed between the inner layer and the outer layer is first obtained. A cell collection portion of the multilayer catheter is identified and the outer layer and the inner layer of the multilayer catheter is removed within the cell collection portion to expose the braid. A sleeve is obtained having an inside diameter larger than an outside diameter of the multilayer catheter and the sleeve is positioned over the cell collection portion.

BRIEF DESCRIPTION OF THE DRAWINGS

To further clarify the above and other advantages and features of the one or more present inventions, reference to specific embodiments thereof are illustrated in the appended drawings. The drawings depict only typical embodiments and are therefore not to be considered limiting. One or more embodiments will be described and explained with additional specificity and detail through the use of the accompanying drawings in which:

FIG. 6a illustrates a weave that may be used for a mesh.
FIG. 6b illustrates a wing of the mesh of FIG. 6a.
FIG. 7a illustrates a weave that may be used for a mesh.
FIG. 7b illustrates a wing of the mesh of FIG. 7a.

DETAILED DESCRIPTION

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Detailed Description does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

Additional advantages of the present invention will become readily apparent from the following discussion, particularly when taken together with the accompanying drawings.

In the following discussion, the terms "distal" and "proximal" will be used to describe the opposing axial ends of the inventive balloon catheter, as well as the axial ends of various component features. The term "distal" is used in its conventional sense to refer to the end of the apparatus (or component thereof) that is furthest from the operator during use of the apparatus. The term "proximal" is used in its conventional sense to refer to the end of the apparatus (or component thereof) that is closest to the operator during use. For example, a catheter may have a distal end and a proximal end, with the proximal end designating the end closest to the operator heart during an operation, such as a handle, and the distal end designating an opposite end of the catheter, such as treatment tip. Similarly, the term "distally" refers to a direction that is generally away from the operator along the apparatus during use and the term "proximally" refers to a direction that is generally toward the operator along the apparatus.

In the following discussion, the terms "high energy state" and "low energy state" will be used to describe the state of a material. "High energy state" denotes a state in which the material has a potential energy greater than a "low energy state." For example, a spring at its relaxed, natural position would be in a "low energy state." When the spring is compressed, the elastic deformation of the spring results in a "high energy state."

Figure 1:
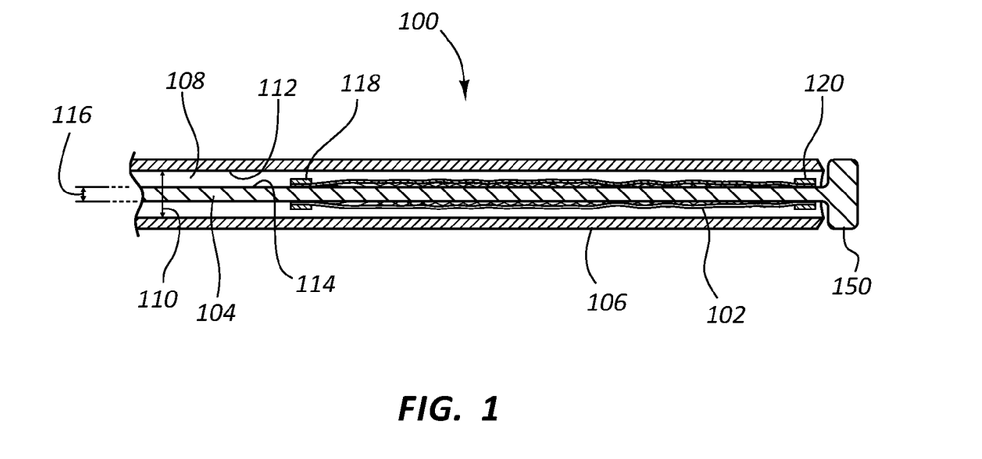
FIG. 1 is a cross-sectional view of a distal end of a cell collection device in an unexpanded state.

FIG. 1 illustrates a distal end an embodiment of a cell collection device 100 having an expandable mesh 102. The cell collection device 100 has a first elongated member 104, the expandable mesh 102, and a sheath 106. The sheath 106 has a bore 108 and the elongated member 104 is disposed within the bore 108. The bore 108 has an inner surface 112 and an inside diameter 110. The elongated member 104 has an outer surface 114 having an outside diameter 116. The mesh 102 is disposed about the elongated member 104 between the outer surface 114 of the elongated member 104 and the inner surface 112 of the bore 108. A stopper 150 may be disposed on a distal end of the elongated member 104.

The stopper 150 may be secured to the elongated member 104 and have an outside diameter greater than the inside diameter of the sheath 106. With the stopper 150 in place, the elongated member 104 is constrained from moving further into bore 108 due to interference between the stopper and the sheath 106. The stopper 150 may be secured to the elongated member 104 through commonly available techniques such as adhesives and crimping.

The cell collection device 100 may be guided to a treatment site using a wire guide and techniques known in the art. The first elongated member 104 may have a longitudinal lumen extending the length of the first elongated member 104 for use in over the wire applications, or may have a side port near the distal end of the cell collection device 100 for use in monorail applications. There may be a space between the first elongated member 104 and the sheath 106 to allow for the wire guide to pass between the first elongated member 104 and the sheath 106. In other embodiments the sheath 106 may have a second side port aligning with the side port for passage of the wire guide. In other embodiments the sheath 106 may be a dual lumen sheath having the bore 108 and a second lumen for tracking over a wire guide. The second lumen may extend the length of the sheath 106 for over the wire applications or have a side port for monorail applications.

The mesh 102 is held in place by a proximal fastener 118 and a distal fastener 120. In some embodiments the mesh 102 may have a membrane 160 coating a distal portion of the mesh 102. The membrane 160 may be a polymer material such as polyurethane. In some embodiments, the proximal fastener 118 and the distal fastener 120 may each comprise a crimped ring, although other mechanisms for fastening the mesh 102 are possible, such as the use of adhesives. The mesh 102 is comprised of a plurality of filaments that have shape memory. In FIG. 1, the mesh 102 and its filaments are shown in a high energy state and are biased to move into a low energy state absent any external constraints. The inside surface 112 of the bore 108 provides a radial constraint to retain the mesh 102 and its filaments in the high energy state. The mesh 102 and the filaments are biased to expand to the low energy state, but cannot extend past the inner surface 112 of the bore 108.

Figure 2:
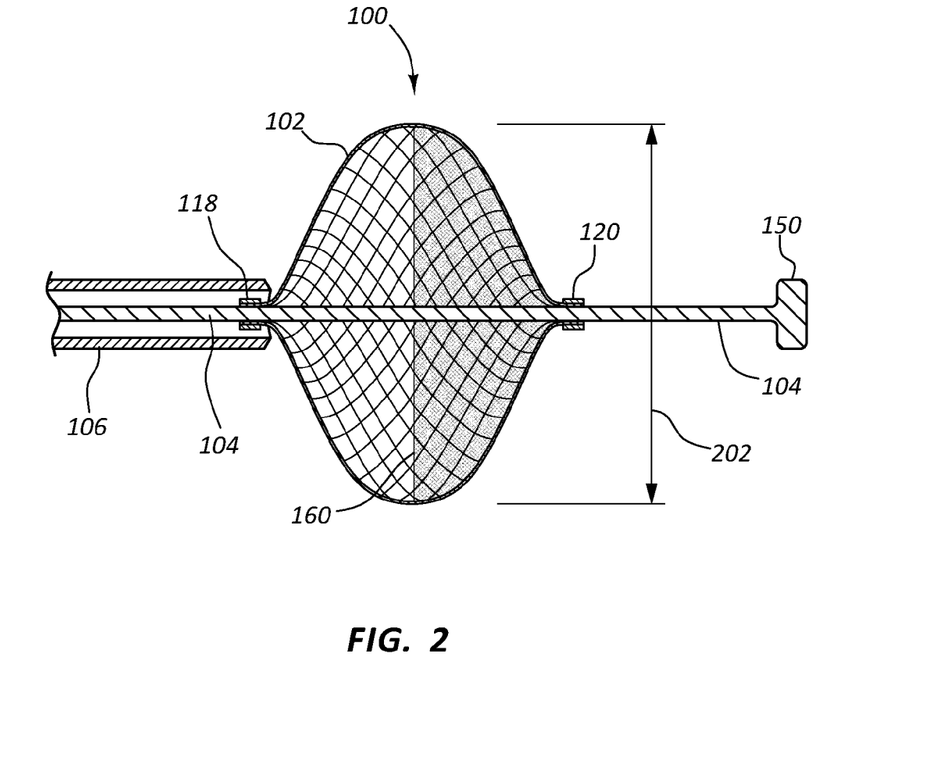
FIG. 2 is a cross-sectional view of the distal end of the cell collection device of FIG. 1 with the cell collection device in an expanded state.

FIG. 2 illustrates the cell collection device 100 of FIG. 1, with the sheath 106 retracted proximally relative to the elongated member 104. With the sheath 106 in the position shown in FIG. 2, the sheath 106 no longer provides a radial constraint to the mesh 102 and its filaments. Absent the radial constraint, the mesh 102 expands from the high energy state of FIG. 1 into the low energy state shown in FIG. 2. In the low energy state the mesh 102 has a deployed diameter 202 that is greater than the inside diameter 110 of the bore 108. As the mesh 102 expands radially it compresses axially. In the embodiment shown in FIG. 2, the distal fastener 120 secures the mesh 102 about the elongated member 104, but still allows the distal fastener 120 to slide axially along the elongated member 104. In embodiments in which the distal fastener 120 comprises a crimped ring, a first ring is placed over the elongated member. The first ring has an inside diameter slightly larger than an outside diameter of the elongated member 104, allowing the ring to slide on the elongated member 104. A second ring is then crimped around the first ring with the mesh 102 placed between the first ring and the second ring. The mesh 102 is compressed between the first and second ring, but is still able to translate axially on the elongated member 104. The proximal fastener 118 is fastened to the elongated member 104 holding the proximal fastener in place 118. In embodiments in which the proximal fastener 118 comprises a crimp ring, the crimp ring is placed over the mesh 104 and crimped, compressing the mesh 104 between the crimp ring and the elongated member 104.

Figure 3:
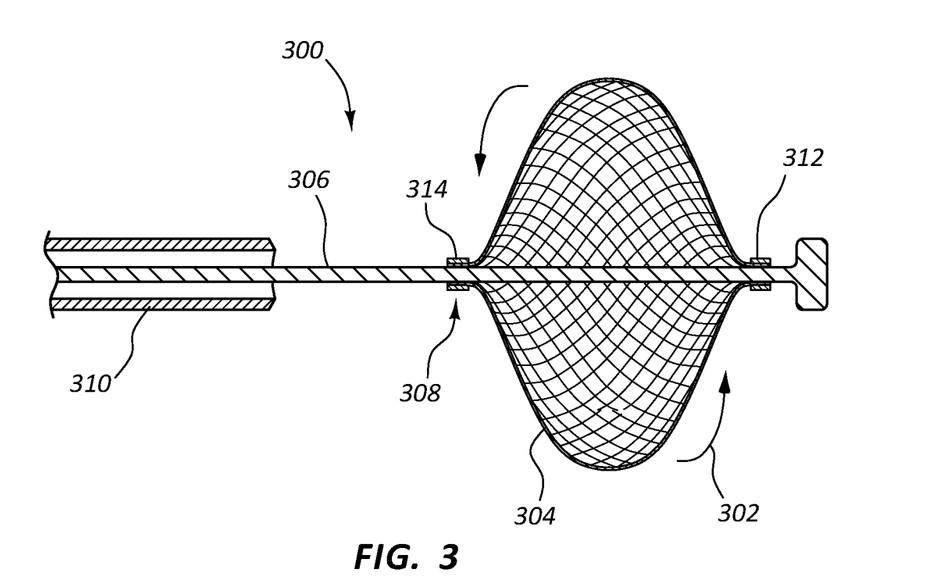
FIG. 3 is a cross-sectional view of a distal end of another embodiment of a cell collection device in an expanded state.

FIG. 3 illustrates an alternative embodiment of a cell collection device 300. When stowed, the cell collection device 300 appears the same as the embodiment of FIG. 1. However, in this embodiment the distal end 302 of a mesh 304 is fastened to an elongated member 306 with a distal fastener 312 such that it does not move axially relative to the elongated member 306. The proximal end 308 is fastened to the elongated member 306 with a proximal fastener 314 and is free to translate axially about the elongated member 306. As a result, when the sheath 310 is retracted, the distal fastener 312 stays fixed in place while the proximal fastener 314 moves distally towards the distal fastener 312 as the mesh expands radially.

The filaments that comprise the mesh 102 are flexible such that when they contact an inner wall of a vessel, the mesh 102 will deform to conform to a shape of the inner wall. The filaments may comprise a material such as a nickel titanium alloy or other shape memory material. The filaments may have a profile having a sharp edge, such as a square. The sharp end facilitates sloughing of cells from the vessel wall when the filament is dragged across it. In some embodiments the mesh may be used for the collection of clots. The clot may pass through the mesh with the mesh in an expanded state and constrained within the mesh with the mesh in the collapsed state.

Figure 4:
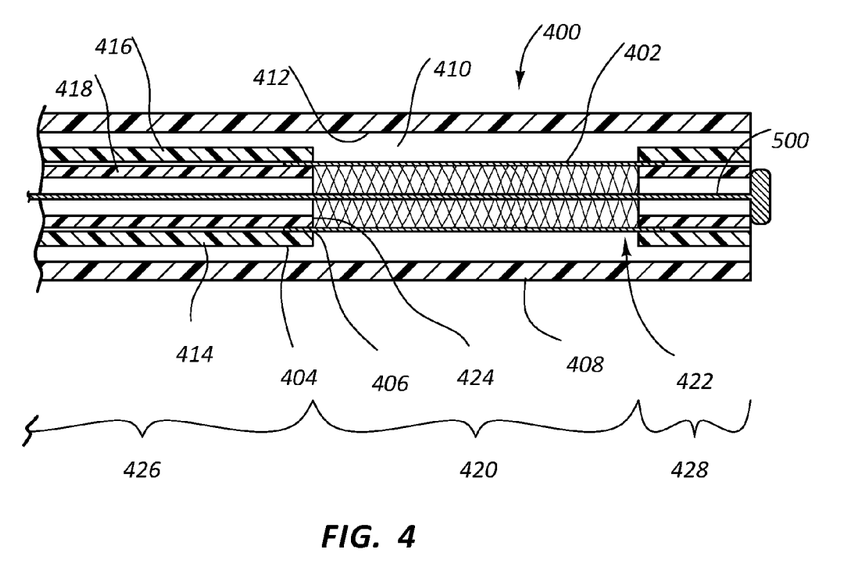
FIG. 4 is a cross-sectional view of the distal end of another embodiment of a cell collection device in an unexpanded state.

FIG. 4 illustrates another embodiment of a cell collection device 400 having an expandable mesh 402. The cell collection device 400 is comprised of a first catheter 404 reinforced by a braid and a second catheter 408 disposed about the first catheter 404. The second catheter 408 may be translated axially relative to the first catheter 404. The second catheter 408 has a bore 410 with an inner surface 412 that faces an outer surface 414 of the first catheter 404.

The first catheter 404 is comprised of an inner layer 416, a braid layer 406, and an outer layer 418. The inner layer 416 and the outer layer 418 may be polymers of the type generally known in the art for use in braided catheters. The braid layer 406 comprises a plurality of filaments woven together to form a tubular braid. The filaments may comprise materials such as stainless steel, nickel titanium alloys, and stiff polymers. In some embodiment, a longitudinal member 500 may be present. The longitudinal member 500 may comprise a filament, such as a suture, attached to the distal end of the first catheter 404.

The first catheter 404 is divided into at least three sections. A braid section 420 has a distal end 422 and a proximal end 424. A proximal section 426 is located proximal to the braid section 420 and a distal section 428 is located distal to the braid section 420. The proximal section 426 and the distal section 428 may each comprise an unmodified portion of the first catheter 404. The braid section 420 is a section of the first catheter 404 with the inner layer 418 and the outer layer 416 removed exposing the braid layer 406.

Figure 5:
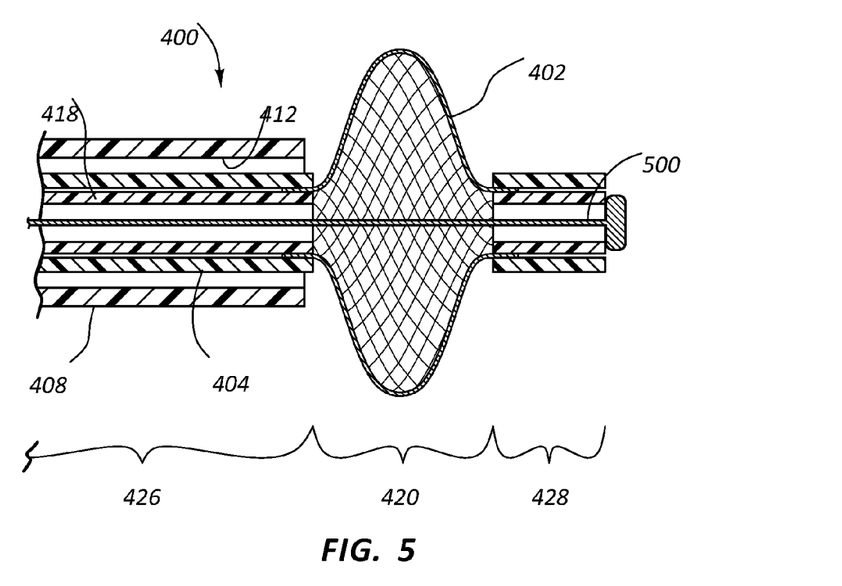
FIG. 5 is a cross-sectional view of the distal end of the embodiment of the cell collection device of FIG. 4 in an expanded state.

Similar to the previously described embodiments, when the braid section 420 is compressed axially, it will extend radially. Because the distal end 422 and the proximal end 424 of the braid section 420 are constrained by the inner layer 418 and the outer layer 416, they will not expand compared to a middle of the braid section 420. FIG. 5 illustrates the cell collection device 400 of FIG. 4 with the sheath 408 moved proximally, exposing the braid section 420 and with the distal section 428 displaced proximally, and the braid section 420 expanded.

In some embodiments the braid layer 406 comprises a shape memory material that is biased to extend outward radially. This bias may exist at the time the first catheter 404 is manufactured, with the braid layer 406 being constrained to a high energy state while the inner layer 418 and the outer layer 416 are formed around the braid layer 406. In other embodiments the braid layer 406 has no bias when the first catheter 404 is formed. A bias may then be applied to the braid layer 406 after the first catheter 404 is formed. For example, in some embodiments the outer layer 416 and inner layer 418 of a braided catheter may be removed and then the braid layer 406 may be expanded by axial compression.

With the braid layer 406 in an expanded state, the braid section 420 may then be heat set so that the expanded state is the low energy state of the braid section 420.

In some embodiments, the high energy state of the braid layer may be the expanded position shown in FIG. 5. In such embodiments an elongated member 500 extends from a location proximal to the braid section 420 to a location distal to the braid section 420. The elongated member is free to move axially in the proximal section 426 and the braid section 420, but is axially constrained in at least the proximal direction by the distal section 428. Movement of the elongated member 500 relative to the proximal section does not affect the proximal section, but causes the distal section 428 to move proximally compressing the braid section 420. The compression of the braid section 420 causes the braid layer 406 to expand, as shown in FIG. 5.

Figures 6A, 6B:
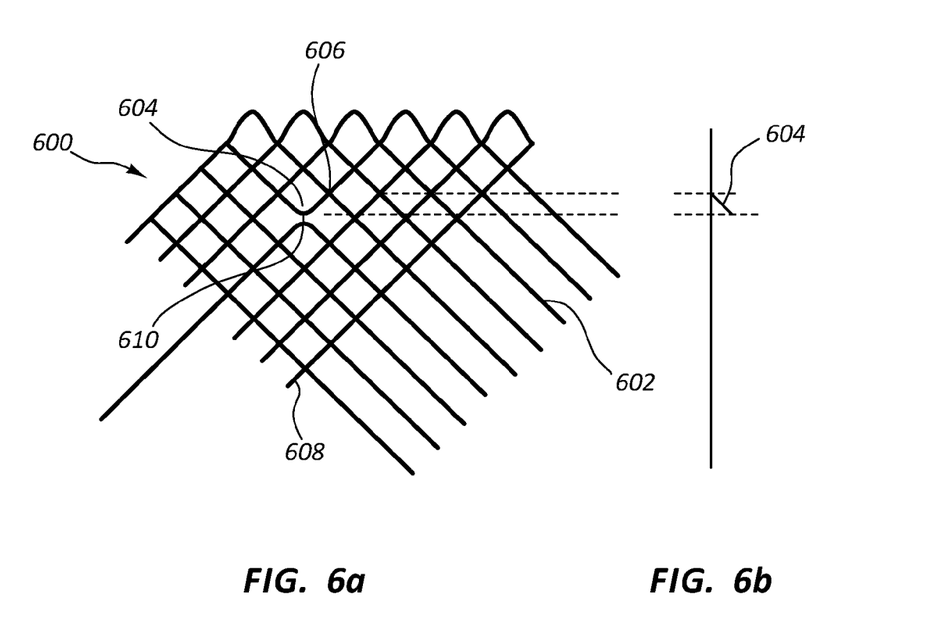

FIGS. 6a and 6b illustrate an alternative weave 600 that may be used for the mesh of a cell collection device. The weave 600 is comprised of a first plurality of filaments 602 winding helically in a first direction and a second plurality of filaments 608 winding helically in a second direction and interwoven with the first plurality of filaments 602. A plurality of wings 604 are woven into the weave. The plurality of wings 604 each comprise a filament 606 that winds in the first direction and then turns to wind in the second direction. This turn results in a corner 610 that is not interwoven with in the weave 600. Because the corner 610 is not interwoven, it may be biased outward, as shown in FIG. 6b. The outward bias of the corner 610 results in a mesh that is more aggressive at removing surface cells than a traditional mesh.

Figures 7A, 7B:
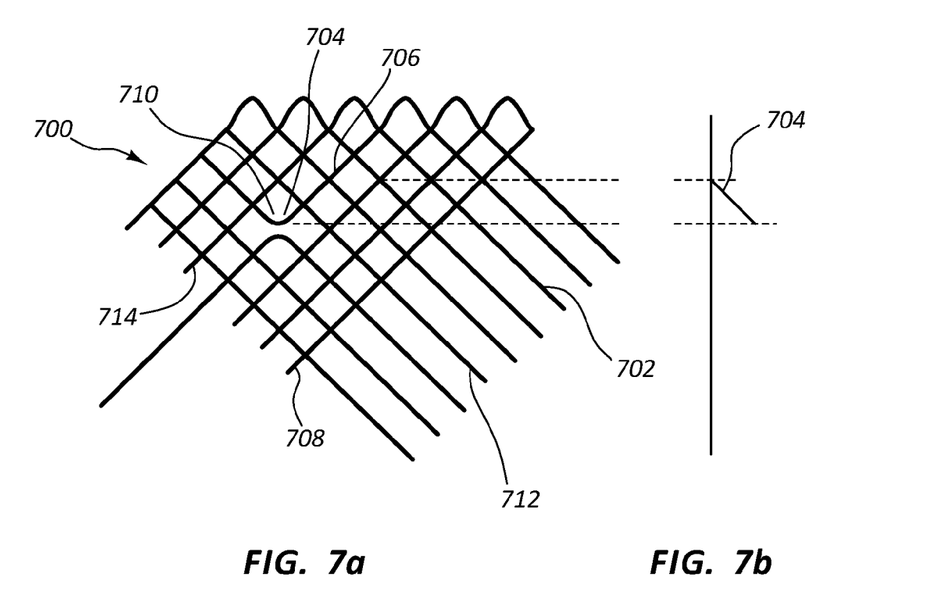

FIGS. 7a and 7b illustrate another alternative weave 700 that may be used for the mesh of a cell collection device. The weave 700 is comprised of a first plurality of filaments 702 winding helically in a first direction and a second plurality of filaments 708 winding helically in a second direction and interwoven with the first plurality of filaments 702. A plurality of wings 704 are woven into the weave 700. The plurality of wings 704 each comprise a filament 706 that winds in the first direction and then turns to wind in the second direction. This turn results in a corner 710 that is not interwoven with in the weave 700. In addition to the corner 710 not being interwoven, the filament may skip being interwoven with adjacent filament 712 and adjacent filament 714. Because the corner is not interwoven with the adjacent filaments 712, 714, it may be biased outward farther than the weave of FIG. 6b as shown in FIG. 7b. The outward bias of the corner 710 results in a more aggressive at removing surface cells than a traditional mesh.

Figure 8A:
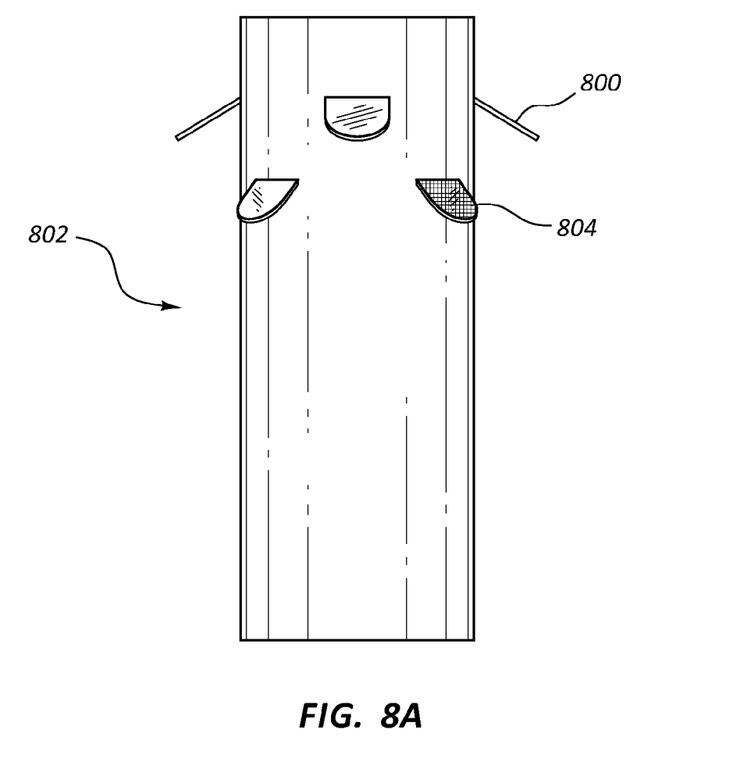
FIG. 8a illustrates a side view of a mesh showing the placement of a plurality of wings.
Figure 8B:
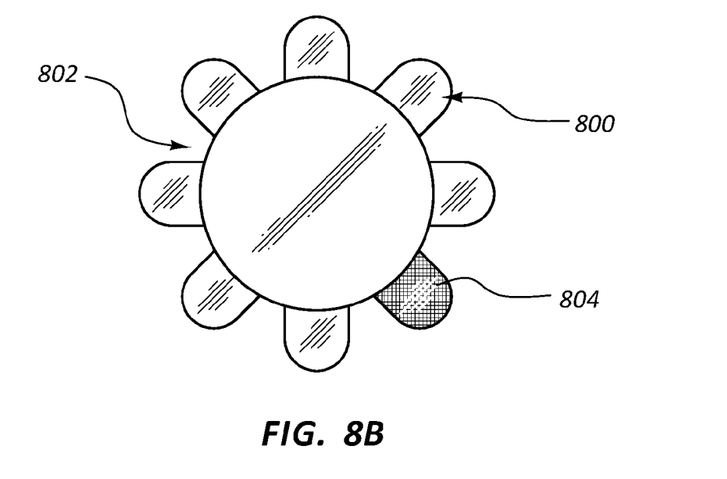
FIG. 8b is a head on view of the mesh of FIG. 8a.
The drawings are not necessarily to scale.

FIG. 8 illustrates an example of the placement of a plurality of wings 800 on a mesh 802. FIG. 8a illustrates a side view and FIG. 8b illustrates a head on view of the mesh 802. The plurality of wings may be arranged at regular intervals about the circumference of the mesh as shown in FIG. 8b such that they will scrape the surface cells evenly. In other embodiments, it may be desirable to focus the cell collection on a particular target area and the plurality of wings 802 may be arranged to engage the target area. In some embodiments, a membrane 804 may be applied to the plurality of wings 800 to aid in the collection of dislodged cells. The membrane 804 guides cells into the interior of the mesh 802 instead of passing through the plurality of wings 800. In some embodiments, the membrane 804 may be applied to locations other than the plurality of wings 800. In one embedment, the membrane 804 is applied to the plurality of wings 800 and to the surface of the mesh 802 except for where the plurality of wings 800 extend from the mesh 802. This embodiment directs the cells dislodged by the plurality of wings 800 wings into the interior of the mesh 802, while the membrane 804 inhibits the cells from passing through the mesh 802 outside of the area in which the plurality of wings 800 extend from the mesh 802. One example of a material suitable for use as the membrane is a silicone coating.

Embodiments of the invention include a method for manufacturing a cell collection device. In the method a multilayer catheter having an inner layer, an outer layer, and a braid comprised of a plurality of woven filaments disposed between the inner layer and the outer layer is obtained. A cell collection portion of the multilayer catheter is then identified. The outer layer and the inner layer of the multilayer catheter are removed within the identified cell collection portion to expose the braid. A sleeve is obtained having an inside diameter larger than an outside diameter of the multilayer catheter. The sleeve is then positioned over the exposed braid.

In some embodiments the plurality of filaments are comprised of a shape memory material. In such embodiment the cell collection portion may be compressed axially causing the plurality of filaments to expand radially into an expanded state. The plurality of filaments are then set to have a shape memory in the expanded state. In some embodiments the sleeve may be slid over the outer surface of the multilayer catheter compressing the plurality of filaments from the expanded state to a unexpanded state wherein the sleeve provides a radial constraint to the plurality of filaments In some embodiments the plurality of filaments are formed of a shape memory material and the braid has a low energy state with an outer diameter greater than an outside diameter of the multilayer catheter. During manufacturing, the braid is radially constrained by the outer layer in a high energy state.

In another embodiment an axial compression mechanism is obtained and inserting in a lumen of the multilayer catheter. The axial compression mechanism extends from a location distal to the cell collection portion to a location proximal to the cell collection portion. The axial compression mechanism may comprise a thread or in other embodiments may comprise a second catheter.

Embodiments of the invention have been primarily described in relation a braided catheter and a sheath. It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed:

1. A cell collection device comprising:
an elongated member having a distal end, a proximal end, and an outside diameter;
a mesh comprised of a plurality of interwoven filaments, the mesh being self-biased to expand outwardly to a deployed diameter that is spaced away from the outside diameter of the elongated member, a first end of the mesh crimped between a first crimp ring and the elongated member so as to prevent movement there between, and a second end of the mesh crimped between a second ring and the elongated member so as to permit translation axially along the elongated member; and
a sleeve disposed about the distal end of the elongated member, the sleeve having a bore with an inside diameter greater than the outside diameter of the elongated member and less than the deployed diameter of the mesh, the sleeve being axially slidable along the elongated member from a first position that radially constrains the mesh to a first radially restrained configuration, and a second position that does not radially restrain the mesh, the second position thereby allowing the plurality of interwoven filaments to expand to the deployed diameter,
wherein the distal end of the elongated member comprises an increased diameter that is configured to occlude the bore of the sleeve when the sleeve is in the first position, wherein the plurality of interwoven filaments each comprise a sharp lateral edge, and wherein at least one of the plurality of interwoven filaments is self-biased to project radially outwardly beyond an outer surface of the mesh so as to form a wing-like shaped projection.

2. The cell collection device of claim 1, wherein the second ring is crimped to a diameter greater than the outside diameter of the elongated member.

3. The cell collection device of claim 1, wherein each of the plurality of filaments is comprised of a material selected from the group consisting of stainless steel, nickel titanium alloys, and a stiff polymers.

4. The cell collection device of claim 1, wherein the second ring is distal to the first ring relative to the elongated member and the second ring moves proximally relative to the elongated member when the sleeve is moved to the second position.

5. The cell collection device of claim 1, wherein the second ring is proximal to the first ring and the second ring moves distally when the sleeve is moved to the second position.

* * * * *